(12) United States Patent
Shimohirao et al.

(10) Patent No.: US 10,206,860 B2
(45) Date of Patent: Feb. 19, 2019

(54) BIGUANIDE PRESERVATION OF PRECIPITATED CALCIUM CARBONATE

(71) Applicant: Colgate-Palmolive Company, Piscataway, NJ (US)

(72) Inventors: Nilza Shimohirao, Sao Paulo (BR); Odete Tieko Yamane, Sao Paulo (BR); Joao Abel Correia, Santo Andre-SP (BR); Katrin Costa, Sao Paulo (BR); Enzo Utima, Sao Paulo (BR); Andre S. David, Sao Paulo (BR)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 14/572,958

(22) Filed: Dec. 17, 2014

(65) Prior Publication Data

US 2015/0164757 A1  Jun. 18, 2015

Related U.S. Application Data

(62) Division of application No. 13/516,355, filed as application No. PCT/US2010/061069 on Dec. 17, 2010, now Pat. No. 8,940,279.

(60) Provisional application No. 61/287,847, filed on Dec. 18, 2009.

(51) Int. Cl.
| | |
|---|---|
| *A61K 8/43* | (2006.01) |
| *A61K 8/19* | (2006.01) |
| *A61Q 11/00* | (2006.01) |
| *A01N 47/44* | (2006.01) |
| *C08G 73/02* | (2006.01) |

(52) U.S. Cl.
CPC ............... *A61K 8/43* (2013.01); *A61K 8/19* (2013.01); *A61Q 11/00* (2013.01); *A61K 2800/524* (2013.01)

(58) Field of Classification Search
CPC ...... A61K 8/43; A61K 8/19; A61K 2800/524; A61K 33/06; A61K 33/10; A61Q 11/00; A01N 47/44; C08G 73/024
See application file for complete search history.

(56) References Cited

U.S. PATENT DOCUMENTS

| | | | |
|---|---|---|---|
| 3,860,648 A | 1/1975 | Diamond et al. | |
| 3,928,555 A | 12/1975 | Gault | |
| 3,935,305 A | 1/1976 | Delaney et al. | |
| 3,966,901 A | 6/1976 | Cullum et al. | |
| 4,001,393 A | 1/1977 | L'Orange | |
| 4,098,878 A | 7/1978 | Baines et al. | |
| 4,748,158 A * | 5/1988 | Biermann | A01N 47/44 514/25 |
| 4,818,783 A | 4/1989 | Shioji et al. | |
| 5,182,101 A | 1/1993 | Wuelknitz et al. | |
| 6,113,887 A * | 9/2000 | Mori | A61K 8/416 424/49 |
| 6,143,065 A | 11/2000 | Freeman et al. | |
| 6,149,894 A | 11/2000 | Yamane et al. | |
| 6,402,824 B1 | 6/2002 | Freeman et al. | |
| 6,777,435 B1 | 8/2004 | Momose et al. | |
| 2003/0044359 A1 | 3/2003 | Wuelknitz et al. | |
| 2006/0275224 A1 | 12/2006 | Burnet et al. | |
| 2008/0233058 A1 | 9/2008 | Maitra et al. | |
| 2009/0087501 A1 | 4/2009 | Cummins | |
| 2009/0088483 A1 | 4/2009 | Anker et al. | |
| 2009/0130715 A1 | 5/2009 | Ochiai et al. | |
| 2009/0202451 A1 | 8/2009 | Prencipe et al. | |

FOREIGN PATENT DOCUMENTS

| | | |
|---|---|---|
| DE | 102004037598 | 2/2006 |
| EP | 1552832 | 7/2005 |
| EP | 1561472 | 8/2005 |
| EP | 1642568 | 6/2010 |
| GB | 1329254 | 9/1973 |
| JP | H03-127718 | 5/1991 |
| JP | H09-295924 | 11/1997 |
| JP | 2003-119340 | 4/2003 |
| JP | 2006-143621 | 6/2006 |
| JP | 2007-176862 | 7/2007 |
| WO | WO 86/002001 | 4/1986 |
| WO | WO 98/056252 | 12/1998 |
| WO | WO 03/016556 | 2/2003 |

OTHER PUBLICATIONS

Di Maiuta et al., 2009, "Microbial Degradation of Formaldehyde in White Mineral Dispersions Preserved with Formaldehyde-releasing Biocides", International Biodeterioration and Biodegradation, 63:769-777.

McNaught et al., 1997, Definition of "Complex" IUPAC Compendium of Chemical Terminology, 2nd ed.

PCT/US2010/061069—ISR and Written Opinion dated Jun. 22, 2011.

PCT/US2010/061069—Written Opinion dated Dec. 6, 2011.

* cited by examiner

*Primary Examiner* — Lezah Roberts

(57) ABSTRACT

Biguanide-preserved precipitated calcium carbonate oral care compositions and methods of manufacture thereof are disclosed.

8 Claims, No Drawings

BIGUANIDE PRESERVATION OF PRECIPITATED CALCIUM CARBONATE

CROSS REFERENCE TO RELATED APPLICATIONS

This application is a divisional of U.S. patent application Ser. No. 13/516,355 filed on 15 Jun. 2012, which is a national stage entry under 35 U.S.C. § 371 of International Patent Application No. PCT/US2010/061069, filed 17 Dec. 2010, which claims priority to U.S. Provisional Patent Application Ser. No. 61/287,847, filed on 18 Dec. 2009, which is incorporated herein by reference.

BACKGROUND

Precipitated calcium carbonate (PCC) is manufactured on a commercial scale for use in a variety of industrial, cosmetic and pharmaceutical products. Generally, precipitated calcium carbonate is made by heating crushed limestone at high temperatures, breaking the raw calcium carbonate into lime (CaO) and carbon dioxide gas ($CO_2$). Addition of the water to the lime (a process called "slaking") yields $Ca(OH)_2$. The slaked lime (or "milk of lime") is treated with carbon dioxide gas. The resulting calcium carbonate precipitates from the aqueous solution, yielding a slurry of precipitated calcium carbonate that can be neutralized, milled, filtered, dewatered and/or dried, as desired.

Slurries of precipitated calcium carbonate are susceptible to microorganisms. To deter microorganisms, a preservative such an aldehyde can be added to the slurry. For example, U.S. Patent Application Publication No. 2009/0088483 discloses combinations of a dialdehyde (such as glutaraldehyde) and a formaldehyde-releasing agent such as (ethylenedioxy)dimethanol. Unfortunately, these preservatives have their limitations. Glutaraldehyde, for example, is unstable at alkaline pH, and is therefore ineffective as a long-term preservative. Furthermore some bacterial, strains metabolize formaldehyde (see, for example, Di Maiuta et al. (2009) *International Biodeterioration & Biodegradation* 63:769-777), permitting bacterial growth even in a treated PCC slurry.

There is a need for improved preservation methods for precipitated calcium carbonate compositions.

SUMMARY

Polymeric biguanides can effectively preserve oral care compositions that include precipitated calcium carbonate. The polymeric biguanide provides lasting antimicrobial action without requiring an aldehyde-based preservative.

Thus, in one aspect, a dry precipitated calcium carbonate composition for use in oral care, or in the manufacture of an oral care composition. The dry precipitated calcium carbonate composition includes, in addition to the precipitated calcium carbonate, a polymeric biguanide such as polyhexamethylene biguanide.

Also provided are precipitated calcium carbonate slurries for use in oral care or in the manufacture of an oral care composition. The slurry includes water, precipitated calcium carbonate, and a polymeric biguanide such as polyhexamethylene biguanide. The slurry is optionally free of other preservatives, such as formaldehyde. The slurry can include one or more other oral care ingredients, such as humectants, inorganic dispersants, bicarbonate salts, pH modifying agents, surfactants, foam modulators, thickening agents, viscosity modifiers, sweeteners, flavorants, colorants, anticaries agents, anticalculus agents, stannous ion sources, zinc ion sources, breath fresheners, antiplaque agents, enzymes vitamins, anti-adhesion agents and combinations thereof. In some embodiments, the concentration of the polymeric biguanide does not exceed 0.04%, For example, in certain embodiments the concentration is between 0.01% and 0.04%.

Also provided are methods of preparing an oral care composition. The methods include combining a pre-formed complex of precipitated calcium carbonate and a polymeric biguanide such as polyhexamethylene biguanide with a composition that includes one or more oral care ingredients chosen from humectants, inorganic dispersants, bicarbonate salts, pH modifying agents, surfactants, foam modulators, thickening agents, viscosity modifiers, sweeteners, flavorants, colorants, anticaries agents, anticalculus agents, stannous ion sources, zinc ion sources, breath fresheners, antiplaque agents, enzymes, vitamins, anti-adhesion agents and combinations thereof.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus of minus a degree of variability to account for errors in measurements. For example, an amount of 10% may include 9.5% or 10.5%, given the degree of error in measurement that will be appreciated and understood by those having ordinary skill in the art.

As used herein, "antibacterial activity" herein means activity as determined by any generally accepted in vitro or in vivo antibacterial assay or test "Anti-inflammatory activity" herein means activity as determined by any generally accepted in vitro or in vivo assay or test, for example an assay or test for inhibition of prostaglandin production or cyclooxygenase activity.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

An oral care composition of the present invention can contain active and/or carrier ingredients additional to those recited above. Classification herein of an ingredient as an active agent or a carrier ingredient is made for clarity and convenience, and no inference should be drawn that a particular ingredient necessarily functions in the composition in accordance with its classification herein. Furthermore, a particular ingredient can serve a plurality of functions, thus disclosure of an ingredient herein as exemplifying one functional class does not exclude the possibility that it can also exemplify another functional class.

According to the present invention, a polymeric biguanide can be added to precipitated calcium carbonate (PCC) as a preservative. The biguanide is optionally added during the initial, preparation of the PCC: after precipitation (e.g. from carbonation of a slaked lime) and before the initial drying. The biguanide preserves the PCC slurry during this process. Furthermore, the inventors have found that the biguanide remains associated with the PCC during this process and after drying. As such, the biguanide not only preserves the PCC, but will also preserve an oral care composition that includes the PCC/biguanide complex.

Polymeric biguanides are polymeric molecules that include multiple biguanide moieties. It is understood that polymerization can generate a population of polymers that vary in size, depending on the number of subunits incorporated. The present invention uses polymeric biguanides that average at least three biguanide moieties per molecule. Generally, an average of at least five biguanide moieties per molecule are included. In certain embodiments, the average number of biguanide moieties is from 5-80, from 5-40, from 6-27, from 9-27, or from 11-18. The biguanide moieties are generally joined by a linker, which can include, for example, an alkyl, a substituted alkyl, a heteroalkyl, a substituted heteroalkyl, an aryl, a substituted aryl, a heteroaryl, or a substituted heteroaryl. The weight average molecular weight of the polymeric biguanide may exceed 1000 Daltons. For example, in certain embodiments, the weight average molecular weight is from 1000-15,000 Daltons; 1000-8000 Daltons; 1.000-5000 Daltons; 1230-5000 Daltons; 1700-5000 Daltons; 2100-5000 Daltons; 2100-3300 Daltons; or 2340-3300 Daltons.

In certain embodiments, a class of polymeric biguanides have the following formula:

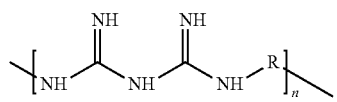

where R is an optionally substituted hydrocarbdiyl group, which may be aliphatic, araliphatic or aromatic, where n is an integer in the range of 5-80, from 5-40, from 6-27, from 9-27, or from 11-18. Examples of suitable R optionally substituted hydrocarbdiyl groups include straight- and branched-chain hydrocarbdiyl groups, such as $C_{1-20}$ alkylene, such as $C_{3-9}$ alkylene (e.g. tetramethylene or hexamethylene) or $C_{5-8}$ cycloalkadiyl (e.g. cyclohexa-1,4-diyl). In certain embodiments, R is of the formula: $(CH_2)_m$, where m is an integer in the range 3-20, or in the range 3-9.

One example of a suitable polymeric biguanide is poly[(hexamethylene)biguanide] (PHMB), also known as polyaminopropyl biguanide and poly(iminoimidocarbonynl) iminohexamethylene hydrochloride. PHMB is commercially available (Arch Chemicals, Inc.).

The polymeric biguanide can be added to a PCC-containing composition at any time. Advantageously, the polymeric biguanide is optionally added when the PCC is initially manufactured, after the formation of the precipitate to form the PCC slurry, and before the slurry is dried. For example, alter the calcium hydroxide solution is treated with an excess of carbon dioxide, forming the PCC, the resulting slurry is fairly alkaline can be neutralized using an acid such as a mineral acid (phosphoric, sulfuric, nitric, and/or hydrochloric, for example) or an organic acid, such as acetic, propionic, or sulfonic acid. A polymeric biguanide in certain embodiments is added to the neutralized PCC slurry prior to drying of the slurry.

In this way, the polymeric biguanide can preserve the PCC against contamination (e.g. bacterial contamination, fungal contamination, or viral contamination) from the time of its initial manufacture. Other preservatives, such as aldehyde-based preservatives, can be omitted from the PCC-containing composition, as their function is provided by the polymeric biguanide. The polymeric biguanide remains associated with the PCC during and after the drying process. The dried PCC-biguanide composition can be resuspended in water, again forming a biguanide preserved slurry useful in an oral care composition.

The polymeric biguanide is added to a concentration sufficient to provide antimicrobial activity. Thus, although higher concentrations of polymeric biguanide could be used, concentrations no greater than 0.04% or no greater than 0.03% are used in certain embodiments. In one embodiment, the concentration of polymeric biguanide is from 0.01%-0.04%. In another embodiment, the concentration of polymeric biguanide is from 0.01% to 0.03%. In another embodiment, the concentration of polymeric biguanide is from 0.025% to 0.03%.

A pre-formed PCC/biguanide complex can be used as an ingredient in an oral care composition such as a dentifrice. The oral care composition may be in the form of a paste, cream, mousse, gel, powder, wash, or the like. The oral care composition in certain embodiments includes one or more other oral care ingredients such as humectants inorganic dispersants, bicarbonate salts, pH modifying agents, surfactants, foam modulators, thicken mg agents, viscosity modifiers, sweeteners, flavorants, colorants, anticaries agents, anticalculus agents, stannous on sources, zinc ion sources, breath fresheners, antiplaque agents, enzymes, vitamins, anti-adhesion agents and combinations thereof. The oral care composition optionally includes at least two, at least three, at least four, at least live, or at least six of the above other oral care ingredients. As but a few examples, the oral care composition can include a humectant; a humectant and a thickener; a humectant, a thickener and a surfactant; a humectant, a thickener, a surfactant, and a fluoride source; a humectant, a surfactant, a fluoride source, and a bicarbonate; a humectant, a surfactant, a fluoride source, a bicarbonate, and an inorganic dispersant; or a humectant, a surfactant, a fluoride source, a bicarbonate, an inorganic dispersant, and flavoring. One or more other oral care ingredients can substitute for or augment any of these ingredients. In embodiments where these oral care ingredients are combined with a pre-formed complex of the PCC bound to the polymeric biguanide, the combination of the polymeric biguanide with the PCC precedes their combination with the other added oral care ingredients.

In various embodiments, toothpastes and tooth gets are formulated containing precipitated calcium carbonate, the polymeric biguanide, at least one humectant, and a carrier. In various embodiments, the toothpaste or tooth gel compositions contain 1% to 70% by weight of PCC, 0.01% to 0.04% of polymeric biguanide; 1% to 70% by weight of at least one humectant, in addition to the carrier.

A humectant is useful, for example, to prevent hardening, of a toothpaste or gel upon exposure to air. Any orally acceptable humectant can be used, including without limitation polyhydric alcohols such as glycerin, sorbitol, xylitol, propylene glycol, mannitol, or low molecular weight PEGs. Most humectants also function as sweeteners. One or more humectants are optionally present in a total amount of 1% to 70%, for example 1% to 50%, 2% to 25%, or 5% to 15% by weight of the composition.

Among useful carriers for optional inclusion in a composition of the invention are diluents (such as water), bicarbonate salts, pH modifying agents, surfactants, foam modulators, thickening agents, viscosity modifiers, sweeteners, flavorants and colorants. One carrier material, or more than one carrier material of the same or different classes, can optionally be present. Carriers should be selected for compatibility with each other and with other ingredients of the composition.

Inorganic dispersants which may be used to stabilize the calcium carbonate slurry include such condensed phosphates as pyrophosphates, tripolyphosphates, trimetaphosphates, tetrametaphosphates, and hexametaphosphates, zinc salts and silicates. Organic dispersants, include polycarboxylates such as polyacrylates, polymethacrylates and polymaleates and polyvinyl alcohol. Such dispersants are known in the art. For example, U.S. Pat. No. 4,818,783 discloses dispersing calcium carbonate in an aqueous medium containing as the dispersant (1) 0.1 to 2 parts by weight of (a) a carboxyl group-containing water-soluble polymer possessing as number average molecular weight in the range of 2,000 to 80,000 and (b) a water soluble condensed phosphate and (2) 0.03 to 1 part by weight of a water soluble anionic modified polyvinyl alcohol respectively based on 100 parts by weight of the calcium carbonate.

In a further embodiment a composition of the invention comprises at least one bicarbonate salt, useful for example to impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like. One or more bicarbonate salts are optionally present in a total amount of 0.1% to 50%, for example 1% to 20% by weight of the composition.

In a still further embodiment a composition of the invention comprises at least one pH modifying agent. Such agents include acidifying agents to lower pH, basifying agents to raise pH and buffering agents to control pH within a desired range. For example, one or more compounds selected from acidifying, basifying, and buffering agents can be included. Any orally acceptable pH modifying agent can be used, including without limitation carboxylic, phosphoric and sulfonic acids, acid salts (e.g. monosodium citrate, disodium citrate, monosodium malate, etc.), alkali metal hydroxides such as sodium hydroxide, carbonates such as sodium carbonate, bicarbonates, sesquicarbonates borates, silicates, phosphates monosodium phosphate, trisodium phosphate, pyrophosphate salts, etc.), imidazole and the like. One or more pH modifying agents are optionally present in a total amount effective to maintain the composition in an orally acceptable PH range.

In a still further embodiment a composition of the invention comprises at least one surfactant, useful for example to improve the compatibility of the other components of the composition and thereby provide enhanced stability, to help in cleaning the dental surface through detergency, and to provide foam upon agitation, e.g. during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxy late, sulfate, sulfonate, phosphate or phosphonate Examples include cocoamidopropyl betaine, N-alkyldiaminoethylglycines (N-laurylaminoethylglycine, N-myristyldiethylglycine, etc.), N-alkyl-N-carboxymethylammonium betaine. 2-alkyl-1-hydroxyethylimidazoline betaine sodium and lauryldimethylaminoacetic acid betaine. One or more surfactants are optionally present m a total amount 0.01% to 10%, for example 0.05% to 5% or 0.1% to 2% by weight of the composition.

In a still further embodiment a composition of the invention comprises at least one foam modulator, useful for example to increase amount, thickness or stability of foam generated by the composition upon agitation. Any orally acceptable foam modulator can be used, including without limitation polyethylene glycols (PEGs), also known as polyoxyethylenes. High molecular weight PEGs are suitable, including those having an average molecular weight of 200,000 to 7,000,000, for example 500,000 to 5,000,000 Of 1,000,000 to 2,500,000. One or more PEGs are optionally present in a total amount of 0.1% to 10%, for example 0.2% to 5% or 0.25% to 2% by weight of the composition.

In a still further embodiment a composition of the invention comprises at least one thickening agent useful for example to impart a desired consistency and/or mouth feel to the composition. Any orally acceptable thickening agent can be used, including without limitation carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, guar, gum arabic and tragacanth, colloidal magnesium aluminum silicate, colloidal silica, alginates, bentonite and other natural clays and synthetic inorganic clays. One or more thickening agents are optionally present in as total amount of 0.01% to 15%, for example 0.1% to 10% or 0.2% to 5% by weight of the composition.

In a still further embodiment a composition of the invention comprises at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of 0.01% to 10%, for example 0.1% to 5% by weight of the composition.

In a still further embodiment a composition of the invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol maltitol, isomalt, acesulfame potassium, glycyrrhizin, perillantine, thaumatin, aspartame, neotame, saccharin and salts thereof, dipeptide-based intense sweeteners, cyclamates and the like. One or more sweeteners are optionally present in a total amount depending strongly on the particular sweetener(s) selected, but typically 0.005% to 5% by weight of the composition.

In a still further embodiment a composition of the invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide flagrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of 0.01% to 5%, for example 0.1% to 2.5% by weight of the composition.

In a still further embodiment a composition of the invention comprises at least one colorant. Colorants herein include pigments, dyes, lakes, strips and agents imparting a particular luster or reflectivity such as pearling agents. A colorant can serve a number of functions, including for example to provide a white or light-colored coating on a dental surface, to act as an indicator of locations on a dental surface that have been effectively contacted by the composition, and/or to modify appearance in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of 0.001% to 20%, for example 0.01% to 10% or 0.1% to 5% by weight of the composition.

Toothpaste and tooth gel compositions are optionally formulated with additional ingredients, including without limitation anticaries agents, additional antibacterial agents, anticalculus or tartar control agents, and the like.

In various embodiments, the compositions comprise an orally acceptable source of fluoride ions, which serves as an anticaries agent. One or more such sources can be present. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride).

As an anticaries agent, one or more fluoride-releasing salts are optionally present in an amount providing a total of 100 to 20,000 ppm, 200 to 5,000 ppm, or 500 to 2,500 ppm, fluoride ions. Where sodium fluoride or monofluorophosphate is the sole fluoride-releasing salt present, illustratively an amount of 0.01% to 5%, 0.05% to 1% or 0.1% to 0.5%, sodium fluoride by weight can be present in the composition.

Advantageously, the toothpaste and tooth gel compositions need not (and, in certain embodiments, do not) include any antibacterial agent beyond the polymeric biguanide. Nevertheless, other antibacterial agents are optionally included or excluded from the compositions of the invention; such antibacterial agents include, for example, halogenated diphenylether compounds, cetyl pyridinium chloride, polyphenols, phenolic compounds, stannous ions, zinc ions, and the like. A non-limiting example of a halogenated diphenylether compound is triclosan.

In another embodiment the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl ether/maleic anhydride (PVME/MA) copolymers, such as those available under the Gantrez™ brand from ISP, Wayne, N.J. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically 0.0 to 50%, for example 0.05% to 25% or 0.1% to 15% by weight.

In various embodiments, the anticalculus system comprises a mixture of sodium tripolyphosphate (STPP) and a tetrasodium pyrophosphate (TSPP). In various embodiments, the ratio of TSPP to STPP ranges 1:2 to 1:4. In certain embodiments, the first anticalculus active ingredient, TSPP is present at 1 to 2.5% and the second anticalculus active ingredient, STPP is present at 1 to 10%.

In one embodiment, an anionic polycarboxylate polymer is present 0.1% to 5%. In another embodiment, the anionic polycarboxylate polymer is present 0.5% to 1.5%, or at 1% of the oral care composition. In one embodiment according to the present invention, the anticalculus system comprises a copolymer of maleic anhydride and methyl vinyl ether, such as for example, the Gantrez S-97 product discussed above.

In various embodiments, the ratio of TSPP to STPP to the synthetic anionic polycarboxylate ranges 5:10:1 to 5:20:10 (or 1:4:2). In one embodiment, the anticalculus system of the oral care composition comprises TSPP, STPP, and a polycarboxylate such as a copolymer of maleic anhydride and methyl vinyl ether at a ratio of 1:7:1. In a non-limiting embodiment, the anticalculus system consists essentially of TSPP present at 0.5% to 2.5%, STPP present at 1% to 10%, and a copolymer of maleic anhydride and methyl vinyl ether present at 0.5% to 1.5%

In another embodiment the composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxy late salts such as stannous formate, acetate, gluconate, lactate, tartrate, oxalate, malonate and citrate, stannous ethylene glyoxide, and the like. One or more stannous ion sources are optionally and illustratively present in a total amount of 0.01% to 10%, for example 0.1% to 7% or 1% to 5% by weight of the composition.

In another embodiment the composition comprises an orally acceptable zinc ion source useful, for example, as an anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of 0.05% to 3%, for example 0.1% to 1%, by weight of the composition.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, α-ionone and the like.

In another embodiment the composition comprises an orally acceptable antiplaque, including plaque disrupting, agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In another embodiment the composition comprises an orally acceptable anti-inflammatory agent. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

Compositions of the inventions optionally contain other ingredients such as enzymes, vitamins and anti-adhesion agents. Enzymes such as proteases can be added for anti-stain and other effects. Non-limiting examples of vitamins include vitamin C, vitamin E and analogs thereof, vitamin B5, and folic acid. In various embodiments, the vitamins have antioxidant properties. Anti-adhesion agents include solbrol, ficin, and quorum sensing inhibitors.

In one embodiment a composition of the invention comprises at least one abrasive in addition to precipitated calcium carbonate. Any orally acceptable abrasive can be used, but type, fineness (particle size) and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically 5% to 70%, for example 10% to 50% or 15% to 30% by weight of the composition. Average particle size of an abrasive, if present, is generally 0.1 to 30 μm, for example 1 to 20 μm or 5 to 15 μm.

SPECIFIC EMBODIMENTS

The invention is further described in the following examples. The examples are merely illustrative and do not in any way limit the scope of the invention as described and claimed.

Example 1

Poly[(hexamethylene)biguanide] (PHMB) is added during the PCC manufacturing process. Specifically, PHMB is added following neutralization of the newly precipitated calcium carbonate slurry with phosphoric acid. The slurry samples are subjected to a Micro Robustness Test (MRT), a challenge test assessing the antimicrobial efficacy of PHMB against a pool of microorganisms including:
*Burkholderia cepacia*
*Enterobacter cloacae*
*Escherichia coli*
*Klebsiella oxytoca*
*Klebsiella pneumoniae*
*Serratia marcescens*
*Providencia rettgeti*
*Pseudomonas aeruginosa*
*Pseudomonas putida*
*Staphylococcus aureus*
*Staphylococcus saprophyticus*
Samples are challenged 3 times at 30 minute intervals with an inoculum of $10^7$ bacteria from the above-listed pool. After 4, 6 and 24 hours, aliquots are tested to measure the log reduction of bacteria. Using these data, the area under the curve (AUC) is calculated. The results are shown in Table 1:

TABLE 1

| PCC slurry | Log reduction | | | AUCN | Aw |
| --- | --- | --- | --- | --- | --- |
| | 4 h | 6 h | 24 h | | |
| With 500 ppm PHMB | 7.2 | 7.1 | 7.7 | 111.7 | 1.013 (23.2° C.) |
| With 250 ppm PHMB | 6.8 | 6.8 | 7.1 | 105.1 | 1.023 (22.8° C.) |

TABLE 1-continued

| PCC slurry | Log reduction | | | AUCN | Aw |
| --- | --- | --- | --- | --- | --- |
| | 4 h | 6 h | 24 h | | |
| With 1% formaldehyde | 7.2 | 7.5 | 8.2 | 171.2 | 1.005 (24.3° C.) |
| Without PHMB (control) | 1.0 | 1.1 | 1.2 | 16.8 | 1.013 (22.1° C.) |

As is evident in the Table, even 250 ppm (0.025%) PHMB very significantly reduces the bioburden. Indeed, PCC preserved with 0.03% PHMB should exhibit antimicrobial robustness comparable to that of PCC preserved with 1.0% formaldehyde, as the 7-log reduction in 24 hours for 250 ppm PHMB is close to the 8-log reduction in 24 hours observed in 1% formaldehyde.

Furthermore, it was observed that the PHMB remains associated with the PCC after the drying process. Although PHMB is water soluble, with the drying process used for PCC (a drum dryer), only water is evaporated; the PHMB remains associated with the PCC.

Example 2

The PHMB-associated PCC is tested for preservative activity in a toothpaste formulation. PHMB-associated PCC is formulated into each of two toothpaste formulas (Formulas A and B) including sorbitol, carboxymethylcellulose, sodium lauryl sulfate, monofluorophosphate, sodium bicarbonate, sodium silicate, flavoring, and water and subjected to an MRT test as described in Example 1.

TABLE 2

| Dental Cream formula | Log reduction | | | MRI |
| --- | --- | --- | --- | --- |
| | 4 h | 6 h | 24 h | |
| Formula A with 0.03% ppm PHMB | 5.1 | 5.4 | 6.4 | 0.86 |
| Formula B with 0.03% ppm PHMB | 4.3 | 5.2 | 6.6 | 0.95 |

Formula A included sorbitol, sodium saccharin, sodium carboxymethylcellulose, sodium monofluorophosphate, sodium bicarbonate, sodium lauryl sulfate, sodium silicate, water. Flavor A, and PCC preserved with PHMB; Formula B included sorbitol, sodium saccharin, sodium carboxymethylcellulose, sodium monofluorophosphate, sodium bicarbonate, sodium lauryl sulfate, sodium silicate, water, Flavor B, and PCC preserved with PHMB. Consistent with the data from Example 1, a PHMB concentration of 0.03% was confirmed to be sufficient to preserve the toothpaste formulas, providing a Micro Robustness Index (MRI) above the target level of 0.75. Furthermore, the PHMB-preserved formulation was aged at 40° C. for 12 weeks and confirmed to be as well preserved as a formaldehyde-preserved formulation during its shelf life.

What is claimed is:

1. A dry complex comprising precipitated calcium carbonate and a polymeric biguanide.

2. The complex of claim 1 wherein the polymeric biguanide averages at least three biguanide moieties per molecule.

3. The complex of claim 1 wherein the polymeric biguanide is poly (hexamethylene)biguanide (PHMB).

4. The complex of claim 1 wherein the polymeric biguanide is present in an antimicrobially effective amount.

5. The complex of claim 1 wherein the polymeric biguanide is present in an amount of 0.01%-0.04% by weight of the complex.

6. The complex of claim 1, wherein the complex can be applied to an oral surface or the complex can be used in a composition that can be applied to an oral surface.

7. The complex of claim 1, wherein the complex is in a composition comprising one or more oral care ingredients selected from the group consisting of humectants, inorganic dispersants, bicarbonate salts, pH modifying agents, surfactants, foam modulators, thickening agents, viscosity modifiers, sweeteners, flavorants, colorants, anticaries agents, anticalculus agents, stannous ion sources, zinc ion sources, breath fresheners, antiplaque agents, enzymes, vitamins, anti-adhesion agents and combinations thereof.

8. The complex of claim 1, wherein the polymeric biguanide has an average molecular weight of 1,000-15,000 Daltons.

\* \* \* \* \*